United States Patent [19]

Meyers et al.

[11] 4,064,013

[45] Dec. 20, 1977

[54] PROCESS FOR PREPARING THIOSTREPTON

[75] Inventors: Edward Meyers, East Brunswick; William H. Trejo, Princeton; Josip Pluscec, Ewing Township; William E. Brown, Princeton, all of N.J.

[73] Assignee: E. R. Squibb & Sons, Inc., Princeton, N.J.

[21] Appl. No.: 748,244

[22] Filed: Dec. 6, 1976

[51] Int. Cl.$^2$ .............................................. C12D 9/14
[52] U.S. Cl. .................................. 195/80 R; 424/117
[58] Field of Search ...................... 195/80 R; 424/117

[56] References Cited

U.S. PATENT DOCUMENTS 2,982,689   5/1961   Donovick et al. .................. 424/117

Primary Examiner—Lionel M. Shapiro
Assistant Examiner—C. A. Fan
Attorney, Agent, or Firm—Lawrence S. Levinson; Merle J. Smith; Donald J. Barrack

[57] ABSTRACT

The antibiotic thiostrepton is produced by culturing aerobically *Streptomyces laurentii* A.T.C.C. No. 31255 in a culture medium containing carbon and nitrogen sources until thiostrepton is accumulated and then recovering the antibiotic from said medium.

2 Claims, No Drawings

PROCESS FOR PREPARING THIOSTREPTON

BACKGROUND OF THE INVENTION

U.S. Pat. No. 2,982,689, issued May 2, 1961, discloses the production of the antibiotic thiostrepton using the microorganism *Streptomyces azureus*, W.C. 3705. The patent states that thiostrepton is an antiinfective medicine having the same general antibiotic spectrum as penicillin. Particular effectiveness of thiostrepton against micrococcic and streptococcic infections is disclosed.

Additional cultures have been previously described as producers of thiostrepton. *Streptomyces hawaiiensis*, A.T.C.C. No. 12,236 was originally reported by Cron et al., *Antibiotics and Chemotherapy*, 6: 63–67 (1956), as a producer of bryamycin. Subsequently, Bodanszky et al., *Journal of Antibiotics*, 16: 76–79 (1963), showed bryamycin and thiostrepton to be identical. Ahmed et al., *Hindustan Antibiotics Bulletin*, 7: 79–80 (1964), reported *Streptomyces* species X-14b as a producer of thiostrepton.

SUMMARY OF THE INVENTION

The antibiotic thiostrepton may be produced by culturing aerobically *Streptomyces laurentii* in a culture medium containing carbon and nitrogen sources until thiostrepton is accumulated and then recovering the antibiotic from said medium.

DETAILED DESCRIPTION OF THE INVENTION

The micororganism used in the present invention is a strain belonging to the genus *Streptomyces* that is isolated from soil. The strain, designated as *Streptomyces laurentii*, has been deposited as No. 31255 in the permanent collection of the American Type Culture Collection, Rockville, Md. A sample of the microorganism can be obtained from said institution.

The following is a description of *Streptomyces laurentii* n. sp. Trejo A.T.C.C. No. 31255. The procedures for characterization of the organism are those recommended by the International Streptomyces Project (ISP); see Shirling et al., *International Journal of Systematic Bacteriology*, 16: 313–340 (1966).

I. Morphology

*Streptomyces laurentii*, A.T.C.C. No. 31255 produces aerial mycelium which is predominantly straight chains of spores with some tendency toward hooks and primitive spirals (atypical RA type). The spores are smooth. The spore color en masse is assignable to the Red series.

II. Behavior on Various Media

The following is a description of colonies of the organism incubated for 10 to 14 days at 28° C on various media.

The color description is from the Color Harmony Journal:

Yeast-Malt Extract Agar

Sporulation is scant as a faint pink blush on white undifferentiated aerial mycelium, reverse color is yellowish-brown to burnt orange. There is a slight rose soluble pigment.

Oatmeal Agar

Sporulation is good, grayish yellow pink (CHM No. 5ec), no distinctive reverse color, no soluble pigment.

Synthetic Salts Starch Agar

Sporulation is good, bisque light rose beige (CHM No. 4ec), reverse color: reddish orange; no soluble pigment.

III. Physiology

No melanin is produced on sodium caseinate-tyrosine agar.

IV. Utilization of Carbon Sources (Cultured in medium of Pridham and Gottlieb at 28° C for 10 days.)

Basal —
Glucose +
Mannitol —
Inositol —
Sorbitol —
Xylose (+)
Arabinose —
Rhamnose —
Fructose —
Raffinose —
Galactose +
Trehalose —
Melibiose (+)
Sucrose +
Lactose +

Legend

+: Utilization positive
—: Utilization negative
(+): Utilization positive, but growth less than glucose control.

The following table presents a comparison of *Streptomyces laurentii* A.T.C.C. No. 31255 with other known thiostrepton producing strains showing that it is distinct from the other organisms. An actual comparison of *Streptomyces laurentii*, A.T.C.C. No. 31255, *Streptomyces azureus*, A.T.C.C. No. 14921, and *Streptomyces hawaiiensis* A.T.C.C. No. 12236 was made. The data for *Streptomyces* species X-14b was obtained from Ahmed et al., *Hindustan Antibiotics Bulletin* 7: 79–80 (1964). The legend is the same as above.

|  | *Streptomyces laurentii* | *Streptomyces azureus* | *Streptomyces hawaiiensis* | *Streptomyces species* |
|---|---|---|---|---|
| Strain No. | ATCC 31,255 | ATCC 14,921 | ATCC 12,236 | X-14b |
| Spore Color Series | Red | Blue | White to Yellow | White |
| Morphology Group | Rectus RA | Spira | Spira | Spira |
| Spore Wall | Smooth | Smooth | Spiny | No report |
| Melanin | — | + | + | —(a) |
| Carbohydrate Utilization: |  |  |  |  |
| Glucose | + | + | + | + |
| Mannitol | — | + | + | (+) |
| Inositol | — | + | + | + |
| Sorbitol | — | — | + | — |
| Xylose | (+) | + | — | (+) |
| Arabinose | — | + | + | — |
| Rhamnose | — | + | + | — |

-continued

|  | Streptomyces laurentii | Streptomyces azureus | Streptomyces hawaiiensis | Streptomyces species |
|---|---|---|---|---|
| Fructose | − | + | + | + |
| Raffinose | − | + | + | + |
| Galactose | + | + | + | (+) |
| Sucrose | + | + | + | + |
| Lactose | + | + | + | + |

[a]The authors do not indicate the medium upon which the melanin determination was made.

The antibiotic thiostrepton is produced by cultivating *Streptomyces laurentii* A.T.C.C. No. 31255 at about 25° C under submerged aerobic conditions in an aqueous nutrient medium containing an assimilable carbohydrate and nitrogen source. The fermentation is carried out for about 22 to 120 hours, preferably about 65 hours, at the end of which time the antibiotic has been formed.

Isolation and purification of the thiostrepton produced can be accomplished using procedures well known is the art; see, for example, U.S. Pat. No. 2,982,689 and Vandeputte et al., *Antibiotics Annual* 1955–1956, pages 560–561.

The following example further illustrates the preparation of thiostrepton from *Streptomyces laurentii* A.T.C.C. No. 31255.

EXAMPLE

A 10 liter batch of *Streptomyces laurentii* A.T.C.C. No. 31255 is fermented in a 14 liter glass vessel with the medium and operating conditions described below:

Stage 1 (Germination)

Inoculum

Tomato paste-oatmeal agar slants are seeded with *Streptomyces laurentii* A.T.C.C. No. 31255. They are incubated 5–7 days and then used to inoculate 100 ml of aqueous soybean meal medium contained in 500 ml Erlenmeyer flasks. The composition of the germination medium is as follows:

|  | Grams |
|---|---|
| Toasted nutrisoy flour | 15.0 |
| Soluble starch | 15.0 |
| Glucose | 50.0 |
| $CoCl_2 \cdot 6H_2O$ | .005 |
| $CaCO_3$ | 10.0 |
| Distilled water to 1000 ml. |  |

The medium, prior to inoculation, is sterilized at 121° C at 15 lbs. steam pressure (psi). The inoculated germination flasks are incubated at 25° C for 72 hours on a rotary shaker, operating at 300 r.p.m. with a 2 inch throw.

Stage 2 (Fermentation)

Inoculum:
500 ml from stage 1

Medium:
Same as stage 1. The glucose, however, is sterilized separately from the other medium ingredients. Thus, 1 liter of 50% aqueous glucose solution is added aseptically to 9 liters of sterile medium containing the other constituents just prior to inoculation.

Incubation 10.5 liters of medium containing the inoculum is incubated for 65 hours. During incubation, the broth is agitated at 350–400 r.p.m. and aerated at the rate of 3.5 to 4.0 liters of air per minute.

Isolation and Purification

After 65 hours of incubation, the fermentation is harvested. The mycelium is separated from the supernatant fluid by centrifugation. Extraction of the antibiotic activity from the mycelial cake is effected by extraction with chloroform. The pooled chloroform extracts are concentrated in vacuo at about 40° C to a residue. The residue is washed with small amounts of methanol to remove some impurities, and then dissolved in a small volume of chloroform. Crystallization is accomplished by the addition of small volumes of methanol.

167 mg of the crystalline material is dissolved in 5 ml of boiling chloroform and the solution is concentrated to half volume. Ethanol is added until cloudiness occurs. By this crystallization step, 153 mg of crystalline thiostrepton is obtained.

That the antibiotic is thiostrepton is shown by the data in the following table:

|  |  | Product of *Streptomyces laurentii* ATCC 31255 | Literature[a] |
|---|---|---|---|
| 1. | Melting point | 250–255° C, dec. | 246–256° C, dec. |
| 2. | Specific rotation 25 $[\alpha]D$ (C=0,6CHCl$_3$) | −60° | −68.5° |
| 3. | Ultraviolet absorption 1% Inflections ($E_{1cm}$) | 225 nm (361) 250 nm (324) 280 nm (208) | 225 nm (520) 250 nm (380) 280 nm (225) |
| 4. | IR- (KBr) - | The sample of thiostrepton from *Streptomyces laurentii* A.T.C.C. No. 31255 gives a spectra equal to that cited in the literature. Amide I and II bands characteristic for a peptide are present. | |
| 5. | Amino acid analysis: |  |  |
|  | threonine | 1.0 | 1.0 |
|  | alanine | 2.19 | 2.0 |
|  | isoleucine | 1.0 | 1.0 |
|  | cystine | traces | traces |

[a]Bodanszky et al., *Journal of Antibiotics*, 16: 76–79 (1963) Vandeputte et al., *Antibiotics Annual*, 1955–1956, 560–561 Bodanszky et al., *Journal of the American Chemical Society*, 86: 2478–2490 (1964).

What is claimed is:

1. A process for producing the antibiotic thiostrepton which comprises culturing aerobically *Streptomyces laurentii* A.T.C.C. No. 31255 in a culture medium containing carbon and nitrogen sources until thiostrepton is accumulated, and then recovering the thiostrepton from the medium.

2. A process in accordance with claim 1 wherein the culturing is carried out at about 25° C.

* * * * *